(12) United States Patent
Win et al.

(10) Patent No.: US 8,282,571 B2
(45) Date of Patent: Oct. 9, 2012

(54) BIAXIAL TEST HEAD

(76) Inventors: Patrick H. Win, Richmond Heights, MO (US); Edwin A. Reed, IV, Lee's Summit, MO (US)

( * ) Notice: Subject to any disclaimer, the term of this patent is extended or adjusted under 35 U.S.C. 154(b) by 0 days.

(21) Appl. No.: 13/341,536

(22) Filed: Dec. 30, 2011

(65) Prior Publication Data

US 2012/0101406 A1    Apr. 26, 2012

Related U.S. Application Data

(63) Continuation-in-part of application No. 12/925,142, filed on Oct. 14, 2010.

(60) Provisional application No. 61/278,935, filed on Oct. 15, 2009.

(51) Int. Cl.
*A61B 5/00* (2006.01)

(52) U.S. Cl. ........................................... 600/556

(58) Field of Classification Search ............ 600/556
See application file for complete search history.

(56) References Cited

U.S. PATENT DOCUMENTS

| | | | |
|---|---|---|---|
| 2,522,309 A | 9/1950 | Simon | |
| 4,711,247 A | 12/1987 | Fishman | |
| 5,097,810 A | 3/1992 | Fishman | |
| 5,551,441 A | 9/1996 | Pitesky | |
| 5,647,371 A | 7/1997 | White | |
| 5,671,753 A * | 9/1997 | Pitesky | 600/556 |
| 5,673,705 A * | 10/1997 | Pitesky | 600/556 |
| 5,692,518 A | 12/1997 | Baker | |
| 5,944,671 A | 8/1999 | White | |
| 6,024,706 A * | 2/2000 | Hsiao | 600/556 |
| 6,095,988 A | 8/2000 | Doll | |
| 6,206,838 B1 | 3/2001 | Doll | |
| 6,322,520 B1 * | 11/2001 | Baik | 600/556 |
| 6,622,730 B2 * | 9/2003 | Ekvall et al. | 128/898 |
| 7,031,432 B2 * | 4/2006 | Geitz | 378/65 |
| 2002/0016527 A1 * | 2/2002 | Hancock | 600/213 |
| 2003/0149331 A1 * | 8/2003 | Geitz | 600/4 |
| 2004/0030237 A1 * | 2/2004 | Lee et al. | 600/414 |
| 2004/0230099 A1 * | 11/2004 | Taylor et al. | 600/204 |
| 2004/0230101 A1 * | 11/2004 | Martin et al. | 600/210 |
| 2006/0167375 A1 * | 7/2006 | Terrassse et al. | 600/556 |
| 2007/0055108 A1 * | 3/2007 | Taylor et al. | 600/210 |
| 2009/0118662 A1 * | 5/2009 | Schnall | 604/20 |
| 2010/0152810 A1 * | 6/2010 | Minogue et al. | 607/48 |

* cited by examiner

*Primary Examiner* — Max Hindenburg
*Assistant Examiner* — Michael C Stout
(74) *Attorney, Agent, or Firm* — Charles McCloskey

(57) ABSTRACT

The present invention provides a device for skin testing. The device includes a handle assembly connected to a cylinder assembly having two mutually parallel and spaced apart cylinder housings. Each cylinder housing connects to at least one testing head assembly that includes a plurality of pins having a plurality of tips positionable against the skin. Each head assembly has a collar and cooperating tip structured to pivot the testing head on two axes only and still apply even pressure to the pins. Each testing head readily inserts into the collar for usage and ejects promptly from the handle using a trigger mechanism. The cylinder housing construction minimizes accumulation of detritus therein.

11 Claims, 13 Drawing Sheets

BIAXIAL TEST HEAD

CROSS-REFERENCE TO RELATED APPLICATIONS

This non-provisional application is a continuation in part application of the pending non-provisional application for patent having the Ser. No. 12/925,142 filed on Oct. 14, 2010 which claims priority to the expired provisional application having the Ser. No. 61/278,935 filed on Oct. 15, 2009 and all are commonly owned by the same inventors, and all disclosures are incorporated by reference.

BACKGROUND OF THE INVENTION

The biaxial test head relates to medical devices used in testing for allergies, and more particularly, but not by way of limitation, to a reusable skin-testing device.

An estimated 50 million Americans suffer from chronic allergies, for example, perennial allergies to cat or dog dander or stinging insects; perennial indoor allergies to dust mites or cockroach allergen and molds; seasonal outdoor allergies to grass, trees or weed pollen; skin allergies these potential allergens or to other materials such as latex; food allergies to milk, soy, eggs, wheat, shellfish, tree nuts, peanuts, fish; allergies to medicine such as penicillin. All ages, sex and racial groups are susceptible to allergies. A person may be tested to determine how he may react to specific allergens. Skin testing is one type of test that determines what allergens may cause an allergic reaction to a patient. Skin testing may involve pricking, puncturing, or scratching the skin with an allergen. In addition, the skin may be tested with histamine or salt water to provide the physician with a control. A positive skin test may show a raised bump (i.e., a wheal) that may be surrounded with redness (i.e., a flare). The size of the bump determines whether the patient is allergic to a particular allergen. Typically the patient may be subjected to from ten to seventy different allergens during initial evaluation. This requires the use of a multi-headed skin-testing device.

Current multi-headed skin testing devices are utilized when skin testing for allergies. One issue with such multi-headed skin testing devices is the occurrence of false positive results. False positive results occur because of an uneven and equal pressure applied to contact points (e.g., tips) with a multi-headed device. For example, some tips have more pressure applied than other tips, resulting in the false positive. Thus, a need exists for an equal and even amount of pressure applied to all the tips of a multi-headed skin-testing device to eliminate false positive results.

DESCRIPTION OF THE PRIOR ART

Allergists and physicians continue to seek better ways to test patients for allergic reaction with the least inconvenience and the maximum efficacy. Patients dread repeated visits for additional allergen testing. Testing multiple allergens simultaneously reduces the number of visits to an allergist and allows for more timely diagnosis and treatment. Various allergy testing devices have appeared over the years. The U.S. Pat. No. 6,322,520 to Bail describes an allergy testing apparatus that compresses two rows of picks into openings. The picks deposit allergens upon a patient. However, the picks generally remain fixed in orientation relative to the handle of the apparatus.

The U.S. Pat. No. 2,522,309 to Simon provides an older testing instrument with an array of pins spaced upon a grid pattern. The pins engage reservoirs of allergen in a cooperating plate. The pins fit into a lid though has limited gripping surfaces for an allergist.

The U.S. Pat. No. 5,097,810 of Fishman describes a testing apparatus that has an actuating member upon a frame. An allergist generally moves the actuating member along the frame thus triggering dispensing of various allergens to a patient. This device though introduces shear force upon the skin of a patient as the actuating member moves side to side.

The U.S. Pat. No. 5,551,441 to Pietsky shows a pick holder apparatus. The apparatus has a plurality of sockets that receive allergen samples. The sockets reside within sidewalls that extend upwardly and outwardly from the device for gripping. An elastic band compresses the sidewalls for a secure fit of the sockets upon allergen sources.

The U.S. Pat. No. 5,647,371 to White illustrates a loading method for skin testing. The method involves a handle with a plurality of picks and a series of openings in a container. Placing the picks upon the openings in registration and then inverting the assembly deposits allergen upon each pick for testing upon removal of the handle from the container.

Mr. Pietsky has a second U.S. Pat. No. 5,673,705, which describes a vial holder that has clamp jaws operably connected to a pair of hand grasp ears. Compression of the ears opens the holder to release any vials therein while a relaxing grip of the ears closes the holder upon vials. As in the prior Pietsky patent, an elastic band provides compression upon the sidewalls to hold the vials in place.

Then the U.S. Pat. No. 5,695,518 to Baker et al. provides a skin test apparatus with a handle joined to a plate that connects to two parallel test elements. Each test element has two ends with gripping jaws that fit upon pins on the ends of the plate. However, the test elements show limited ability to pivot.

The U.S. Pat. No. 6,095,988 to Doll et al. describes an autoloader for a skin test system that has a plurality of spaced picks that engage similar spaced reservoirs. The picks collect testing agent thereon for application to a patient's skin for testing. This load has picks joined to it and detachable reservoirs unlike the present invention.

Mr. Doll et al. has a second patent, U.S. Pat. No. 6,206,838 upon another version of the autoloader. This autoloader has a handle with two parallel feet that fit within chambers of skids. Opposite the chambers, each skid has a plurality of picks where each pick engages a reservoir to pick up testing agent. The skids allow for detachment of gangs of picks from the handle.

The U.S. Pat. No. 5,944,671 to White describes another test applicator with a handle that engages a separate plurality of picks. The handle has a hook like appendage that fits into a holder of the picks securing the pick holder to the handle. The appendage slides under action of a biasing member within the handle to lock and to unlock from the holder.

The U.S. Pat. No. 4,711,247 to Fishman provides an allergy testing method using a gang of pricking devices. The pricking devices connect to two bars and pass through a third bar. The bars connect to perpendicular posts proximate the ends of the bars, similar to a fence. Mutually compressing the two outer bars, outwardly of the posts, drives the pricking devices to deliver allergen to a patient.

And, the U.S. Pat. Pub. No. 2006/0167375 to Terrassse et al. illustrates a skin testing kit. The kit has an instrument that holds three testing bodies. Each body has a round sharp edge with a centered multi-point needle packaged with allergen inside of a blister. Upon pressing the handle, the sharp edge breaks the blister, releasing allergen for pricking upon the skin of a patient.

The present invention overcomes the disadvantages of the prior art and provides a biaxial test head that pivots upon two axes, has single piece handle construction, rolling ball setscrew in the handle but not the tip of the head, and a quick release mechanism in the handle but not the tip of the head. The biaxial test head allows for insertion of a head by a user by pressing the uppermost portion of the head into the handle and then pivoting on two axes but not rotation of the head relative to the handle.

SUMMARY OF THE INVENTION

Generally, the biaxial test head has a reusable handle with two cylinder housings, or legs, that each receive testing heads having four multi-pronged needles for application of allergen. Each testing head has a male ball hex with a select hexagonal geometry and a partially flattened top outwardly from the main portion of the testing head. Each cylinder housing has an opening downwardly from the remainder of the handle. Each opening has a hexagonal shape for admission of the ball hex of a testing head. The opening opens into a collar that fits within a cylindrical sleeve. The collar has a quick release mechanism proximate the opening, preferably three equiangularly spaced balls. Upwardly from the quick release mechanism, the sleeve has a tapped aperture that receives a set screw threaded therein. The set screw retains a ball at the bottom of the aperture, away from the handle, that abuts the top of the ball hex of the testing head.

The hexagonal opening and hexagonal tip of the head cooperate with the quick release mechanism so the head tips left to right, and front to back slightly but does not rotate about an axis coaxial with the centerline of a cylinder housing. The biaxial movement accounts for skin and body variations of a patient being tested using the device. And, the set screw holds a ball against the top of the head allowing for some movement but upon pressing the set screw downwardly, that is, away from the handle, the ball pushes the top downwardly, ejecting the top, or ball hex, of the head from the quick release mechanism for changing the head.

The present invention provides a device and method for skin testing. The device includes a handle assembly connected to a cylinder assembly having a first cylinder housing and second cylinder housing. Each cylinder housing is connected to at least one testing head assembly. The testing head assembly includes a plurality of pins positionable against the skin and a socket assembly structured and operable to pivot the testing head assembly to apply equal and even pressure to all the pins.

Further, the method provides for testing patients to an allergen by positioning a skin-testing device on the surface of the skin. The device has a handle assembly connected to a cylinder assembly, the cylinder assembly being structured and operable to attach to a plurality of testing head assemblies. The testing head assemblies include a plurality of pins structured to be coated with an allergen. The pins being structured and operable to prick the surface of the skin. The testing head assemblies further include a release mechanism structured and operable to pivot the testing head assembly. The method further including a step of pivoting the testing head assembly horizontally to apply equal and even pressure to the pins.

There has thus been outlined, rather broadly, the more important features of the invention in order that the detailed description thereof that follows may be better understood and that the present contribution to the art may be better appreciated. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the biaxial test head is to provide a device that can readily collect, transport, and deliver allergens to the skin of a patient.

Another object of the biaxial test head is to provide such a device that produces less skin damage than existing devices.

Another object of the biaxial test head is to provide such a device that readily provides complete control of the device by the practitioner before, during, and after usage.

Another object of the biaxial test head is to provide such a device that has a tip arrangement that limits rotation of the working tips of the device against unwanted rotation.

Another object of the biaxial test head is to provide such a device that has a tip arrangement that avoids inadvertent adherence to skin tissue during usage.

Another object of the biaxial test head is to provide such a device that has a low cost of manufacturing so the practitioners and clinics can readily purchase the inserter through existing medical supply outlets.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
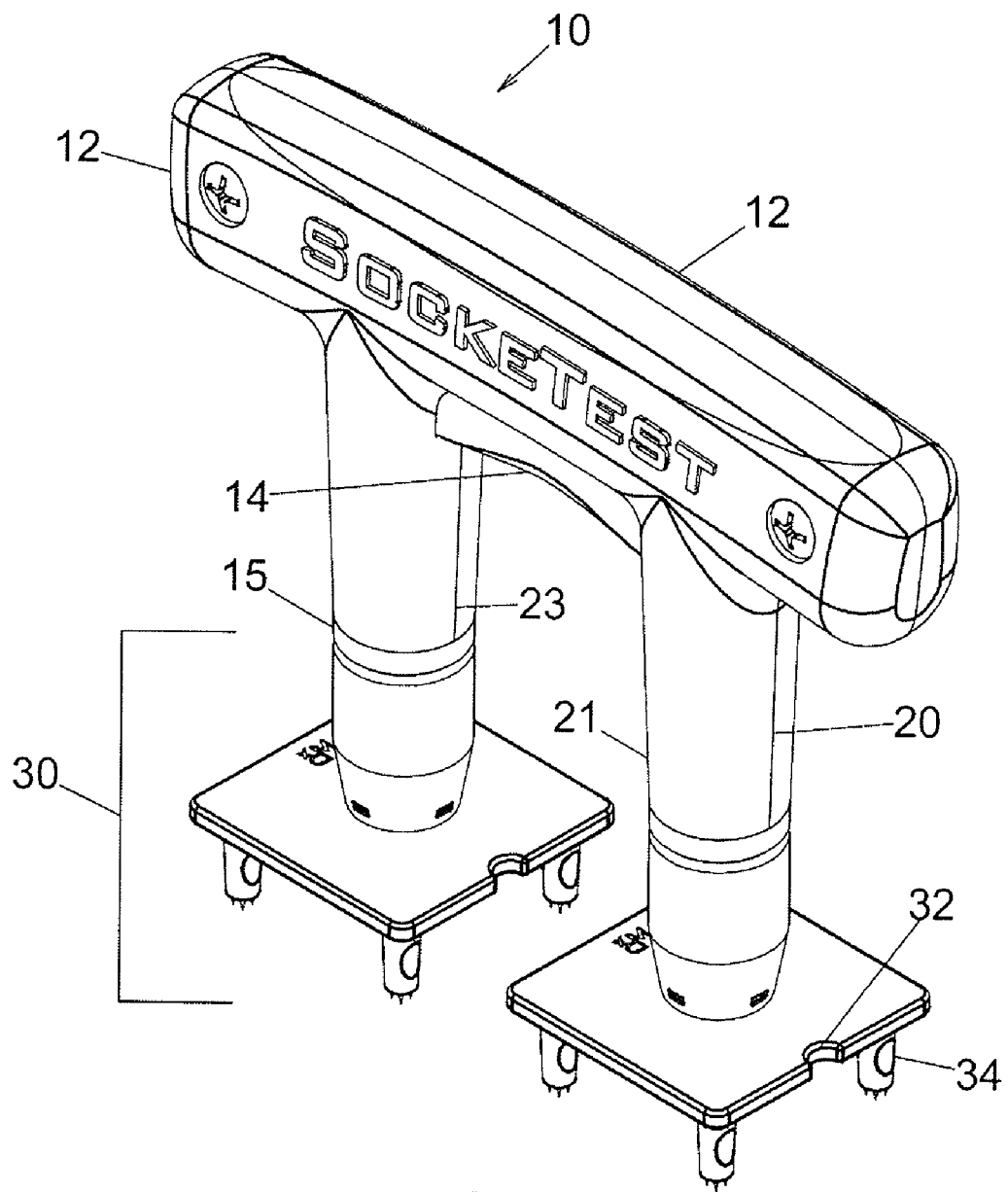
FIG. 1 illustrates a skin-testing device.

The present invention overcomes the prior art limitations by providing a test head of an allergy testing instrument that pivots upon two axes without compromising the test allergens thereon. Referring now to FIG. 1, it shows a skin-testing device 10 used by a health care worker or practitioner (e.g., nurse, physician and the like) to test a patient (e.g., human or animal) for sensitivities to certain allergens, (e.g., allergies). The skin-testing device 10 includes a handle 12, a trigger mechanism 14, a collar 15 located between a cylinder assembly 20, and a testing head assembly 30. The handle 12 may be manufactured by injection molding using an impact resistant acrylonitrile butadiene styrene ("ABS") plastic, or other polymer material that provides lightweight and durability.

In one embodiment, the skin testing device 10 has the handle 12 connected to the cylinder assembly 20. This and subsequent figures show the name Socketest® upon the handle however, the handle is not restricted to that manufacturer. Cylinder assembly 20 includes a first cylinder housing 21 and a second cylinder housing 23. The first cylinder housing 21 and the second cylinder housing 23 are separated by a predetermined distance. Each cylinder housing 21, 23 is operatively connected to one of two testing head assembly 30. In one embodiment, cylinder housings 21, 23 are operatively connected to at least two testing head assemblies 30. The testing head assembly 30 includes a plurality of pins 34, where each pin has a plurality of tips (shown in FIG. 4C) and a notch as at 32. Each testing head itself as shown in this figure has a symbol WRx™ however, each head is not restricted to that manufacturer.

Other embodiments of the skin-testing device 10 may be used. For instance, an embodiment may include more than two cylinder assemblies 20 and more than two testing head assemblies 30. For example, the skin testing device 10 may include two handles 12 structurally arranged in an X-type pattern, with a cylinder housing 20 structurally connected to each of the four ends of the X. A pair of testing head assemblies 30 are structurally and operably connected to the end of each of the four cylinder housings 20, not shown in this figure.

Figure 2A:
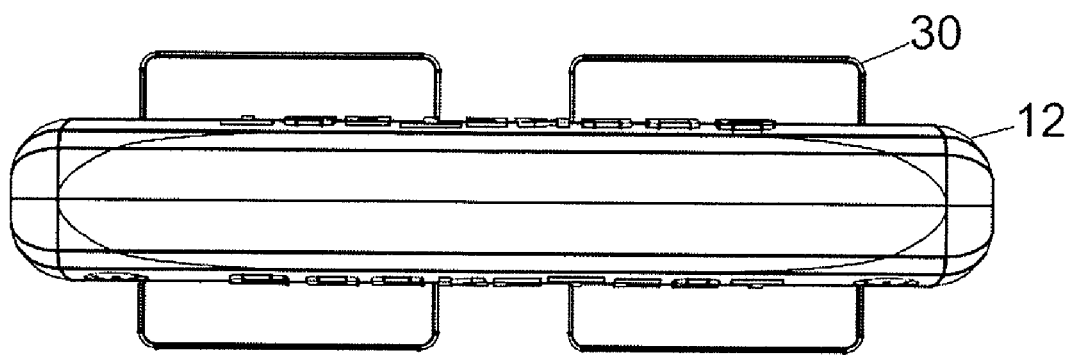
FIG. 2A shows a top view of the skin-testing device.
Figure 2B:
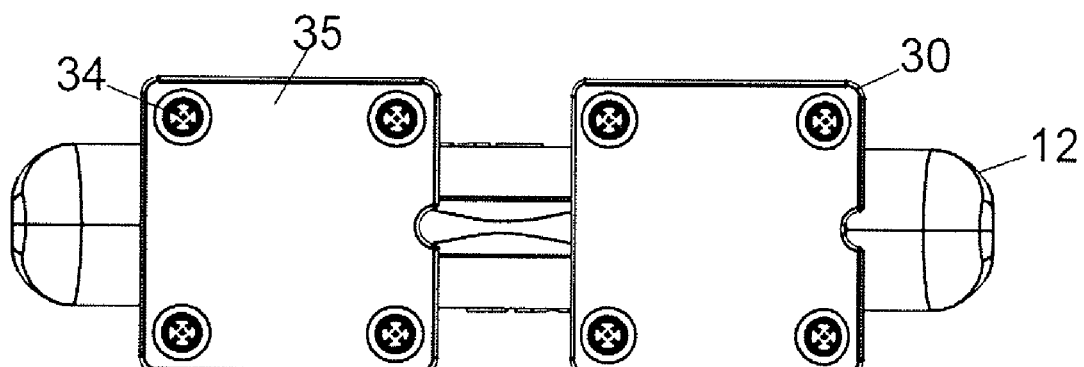
FIG. 2B describes a bottom view of the skin-testing device.

FIG. 2A shows a top view of the skin-testing device. FIG. 2B shows a bottom view of the skin testing device having at least two testing head assemblies 30 connected to the device, where each testing head assembly 30 has four pins 34. In one embodiment the four pins 34 are arranged proximate the four corners of a baseplate 35. In other embodiments, more than four pins 34 may be utilized in various configurations. For instance, pins 34 may be located at each corner of the baseplate 35, and one pin 34 may be located in the center of the baseplate 35 (e.g., five pins). Or, there may be multiple rows of pins. For instance, two rows of pins 34 may be utilized, where each row is separated a predetermined distance from an adjacent row, and each row has at least three pins 34 (e.g., six pins). Alternatively, three rows of pins 34 may be utilized, where each row is separated a predetermined distance from an adjacent row, and each row has at least three pins 34 (e.g., nine pins).

Figure 3A:
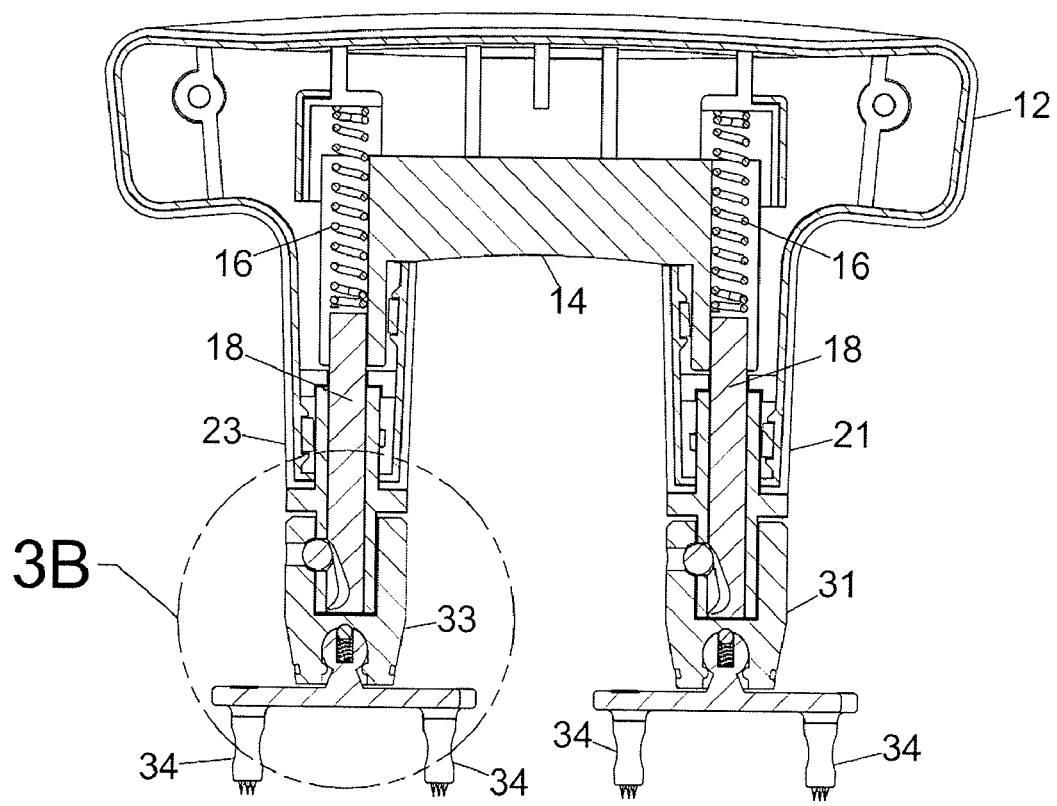
FIG. 3A provides a cross-section of the skin-testing device.
Figure 3B:
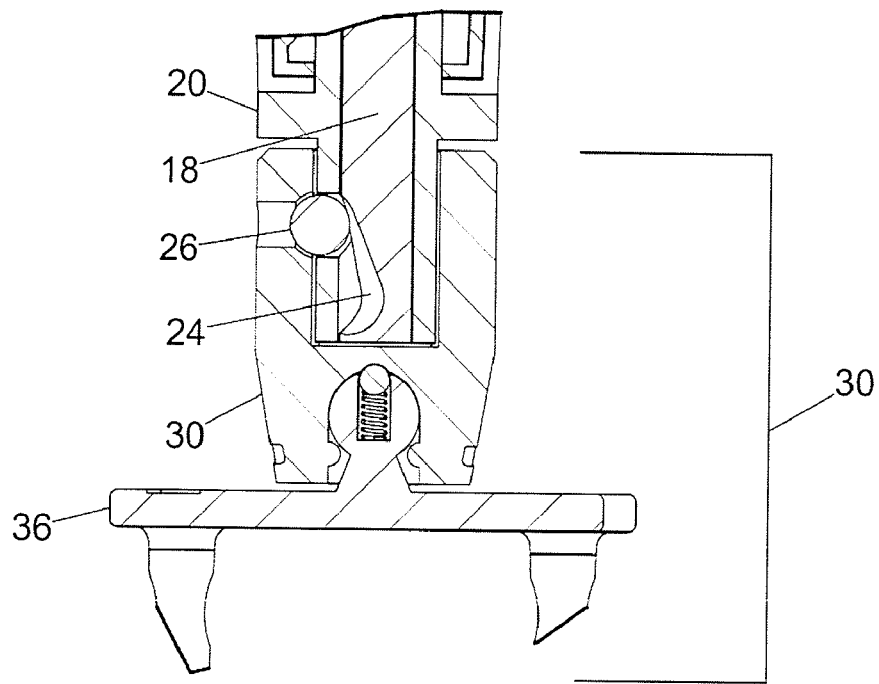
FIG. 3B describes an enlarged view of a cylinder housing connected to a testing head assembly shown in FIG. 3A.

FIG. 3A shows a cross-section of the skin testing device shown in FIG. 1, and FIG. 3B shows an enlarged view of a cylinder housing connected to a testing head assembly shown in FIG. 3A. The handle 12 is connected to the cylinder assembly 20, the cylinder assembly 20 having a first cylinder housing 21 and a second cylinder housing 23. The first cylinder housing 21 is removeably connected to a testing head assembly 31, and the second cylinder housing is removeably connected to a testing head assembly 33. Each cylinder housing 21, 23 includes a cylinder bearing shaft 18 having a pocket 24. The cylinder bearing shaft 18 may be manufactured from high-grade stainless steel. The pocket 24 is structured to receive a bearing 26 (e.g., a 4 mm ball bearing and the like). The handle 12 further includes a trigger mechanism 14 having a biasing device 16 (e.g., a spring, a pneumatic cylinder, and the like), where the biasing device 16 is connected to the cylinder bearing shaft 18. The biasing device 16 maybe manufactured from a high-grade stainless steel, a corrosion resistant grade of steel, and manufactured so that the biasing device 16 has the kinematic properties of a compression spring. Trigger mechanism 14 is structured and operable to compress the biasing device 16 such that the cylinder bearing shaft 18 receives the bearing 26 in the pocket 24.

In one embodiment, the testing head assembly 30 may be removed and replaced. For example, the testing head assembly 30 may be disconnected from the cylinder housing 21 when the trigger mechanism 14 is compressed. Compressing trigger mechanism 14 causes the biasing device 16 to be compressed. The compressed biasing device 16 moves the cylinder bearing shaft 18 longitudinally along a vertical axis of the cylinder housing 21, thereby resulting in the bearing 26 moving into the pocket 24.

Figure 4A:
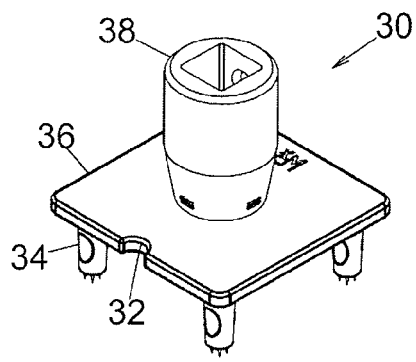
FIG. 4A provides a testing head assembly.
Figure 4B:
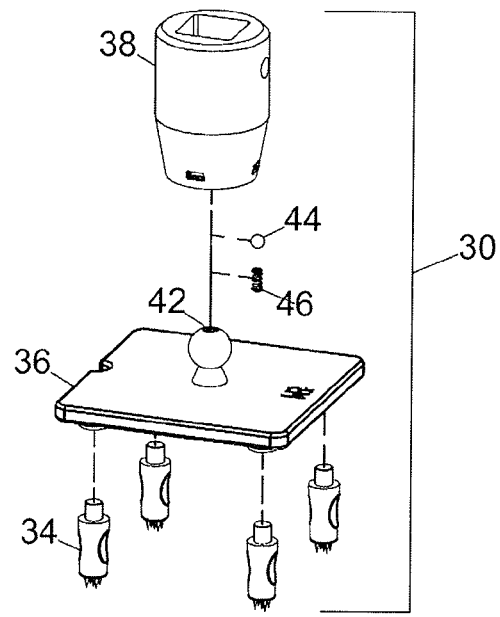
FIG. 4B illustrates an exploded view of the testing head assembly shown in FIG. 4A.

FIG. 4A shows the testing head assembly 30, and FIG. 4B shows an exploded view of the testing head assembly 30. The testing head assembly 30 may be manufactured, for example, from titanium, machined from surgical-grade stainless steel, and the like. The testing head assembly 30 is reusable and may be sterilized or autoclaved. The testing head assembly 30 includes a testing head 38, a baseplate 36 having a notch 32, and a socket assembly 42. Further, each baseplate itself as shown in this and subsequent figures has a symbol WRx™ however, each baseplate is not restricted to that manufacturer. Notch 32 serves to align the testing head assemblies 30 in an allergen tray (described below in FIG. 9 and FIG. 10). The socket assembly 42 has a ball bearing 44 and a spring 46, and the socket assembly 42 is disposed within the testing head 38. Further, the baseplate 36 is connected to a plurality of pins 34.

Figure 4C:
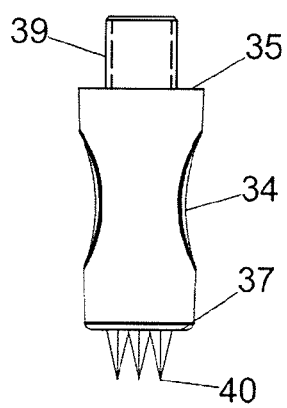
FIG. 4C shows a pin having a plurality of tips.

FIG. 4C shows one pin 34. The pin 34 has a first end 35 and a second end 37, where the first end 35 includes a male screw portion 39, and the second end 37 has a plurality of tips 40. Pin 34 has a plurality of concave indentations and, further, the surface of pin 34 is knurled for an easy grip. The male screw portion 39 turns into a female screw portion (not shown) of baseplate 36. Thus, the pin 34 is removably connected to the baseplate 36. Pin 34 is structured to be reusable and may be sterilized or autoclaved. Further, pin 35 is structured to be independently coated with a selected allergen. The allergen may be one of a plant allergen (e.g., a tree pollen, a weed pollen, and the like), a latex allergen, an animal allergen (e.g., a dog dander allergen, a cat dander allergen, a bee sting allergen, and the like), an insect allergen (e.g., a cockroach allergen, a dust mite allergen and the like), a food allergen (e.g., a soy allergen, a milk allergen, an egg allergen, a wheat allergen, a shellfish allergen, a peanut allergen, a nut allergen and the like), a medicine allergen (e.g., a penicillin allergen), a mold allergen, a fungus allergen, and the like.

Figure 4D:
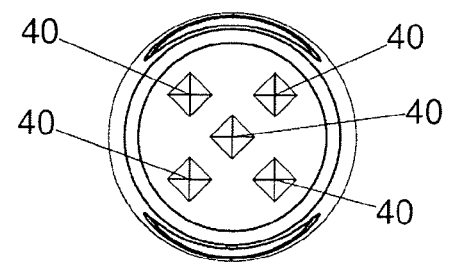
FIG. 4D describes one arrangement of the tips for the pin shown in FIG. 4C.

FIG. 4D shows one arrangement of the tips for the pin 34 shown in FIG. 4C. The plurality of tips 40 are arranged in a X shaped pattern or a cross-configuration. One embodiment has at least five tips 40, but various numbers of tips may be used (e.g., three tips, six tips, nine tips and the like) depending on the layout and arrangement of the tips.

Figure 5:
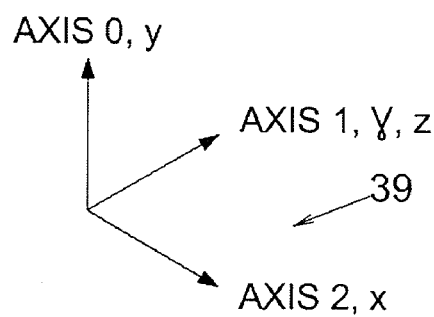
FIG. 5 illustrates the axes of movement of the testing head assembly.
Figure 5:
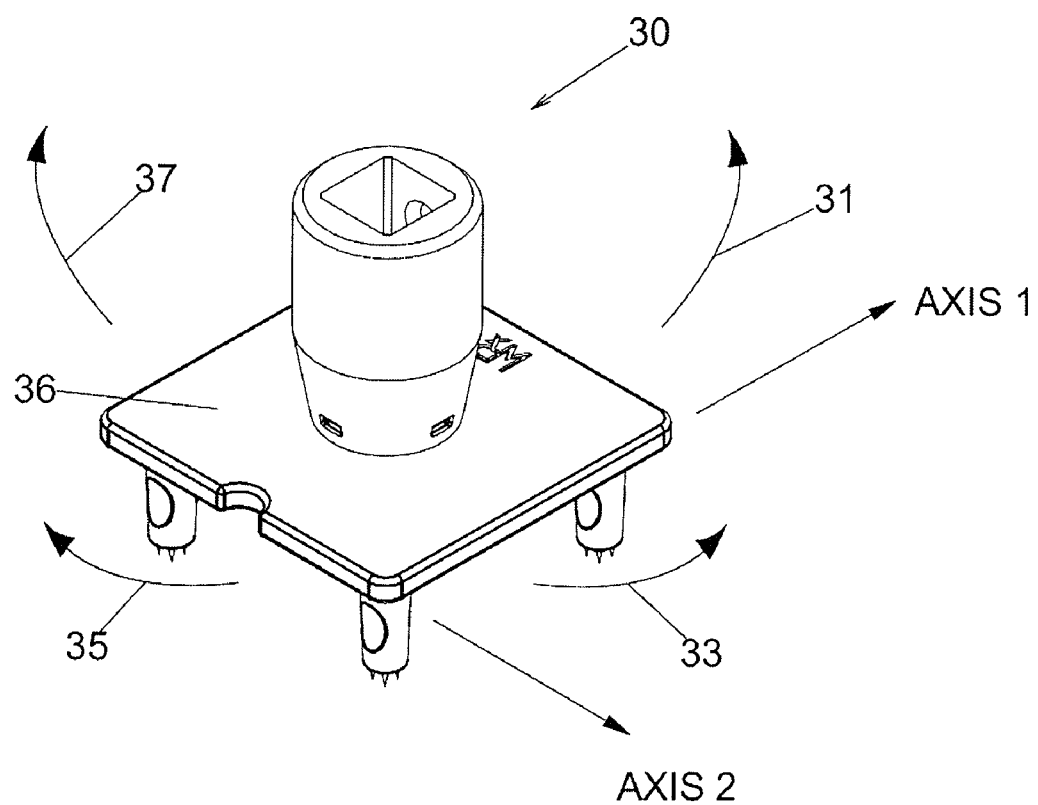

FIG. 5 shows axes of movement 39 of the testing head assembly 30. The axes of movement 39 has an axis-1 (e.g., corresponding to a z-axis), an axis-2 (e.g., corresponding to a x-axis), and an axis-0 (e.g., corresponding to a y-axis). The axes of movement 39 are in relation to the horizontal baseplate 36. Testing head assembly 30 pivots along the axis-2, as indicated by arrows 33, 37. Furthermore, testing head assembly 30 pivots along the axis-1, as indicated by arrows 31, 35. The testing head assembly 30 is structurally and operational to pivot relative to a horizontal axis in the range of about five degrees to about ten degrees. In one embodiment, the testing head assembly 30 may pivot relative to the horizontal axis in the range of about one degree to about twenty degrees.

Figure 6A:
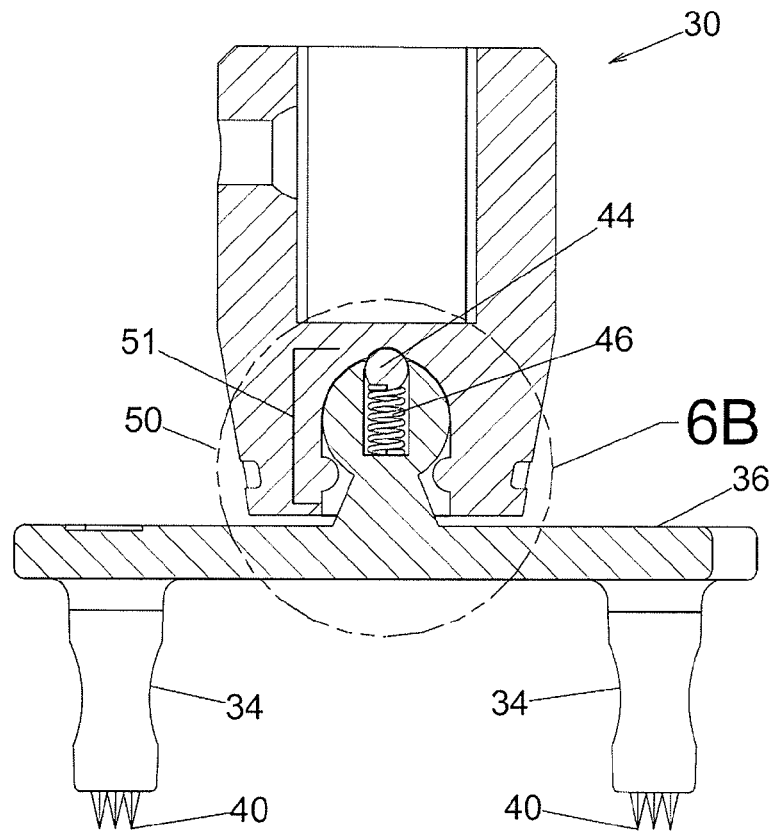
FIG. 6A provides a testing head assembly having a socket assembly.

FIG. 6A shows the testing head assembly 30 has a socket assembly 50. The socket assembly 50 has a release mechanism 51 that includes a ball bearing 44, a spring 46, and a slot 52 (shown in FIG. 6B). The slot 52 is located coaxial to a longitudinal axis of the cylinder housing 20. The ball bearing 44 is connected to the spring 46, and the ball bearing 44 is structured to rest in the slot 52 located in the testing head assembly 30.

Figure 6B:
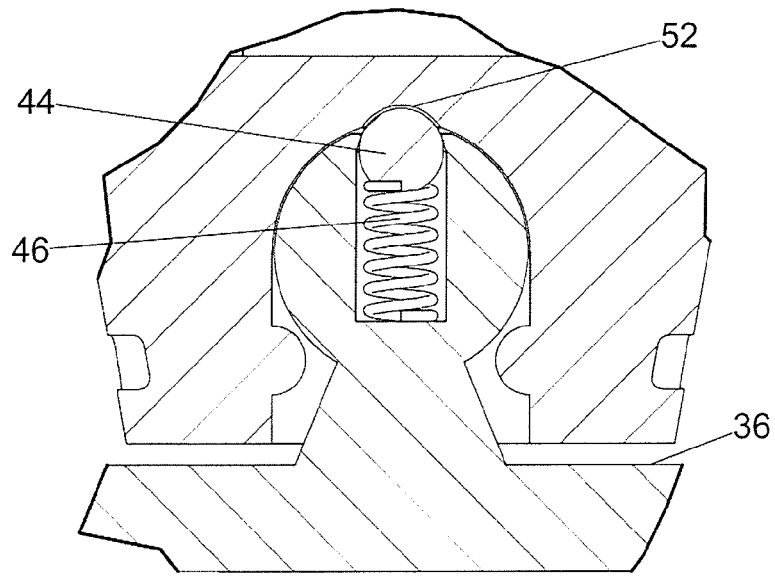
FIG. 6B shows an enlargement of the socket assembly of FIG. 6A identifying a release mechanism in a locked position.

FIG. 6B shows an enlargement of the socket assembly 50 when the release mechanism 51 is in a locked position. The release mechanism 51 is in a locked position when the ball bearing 44 is positioned in the slot 52. When in a locked position, the baseplate 36 is in a horizontal position, that is, perpendicular to the length of a cylinder housing, and thus the testing head assembly 30 cannot pivot.

Figure 7A:
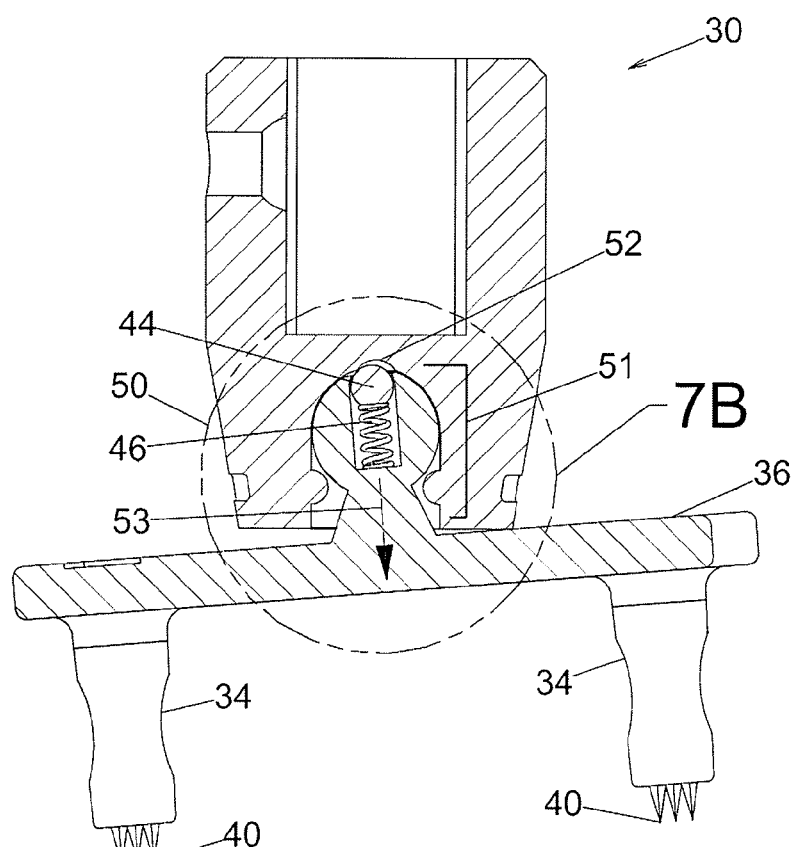
FIG. 7A provides the release mechanism of FIG. 6A in an unlocked position.
Figure 7B:
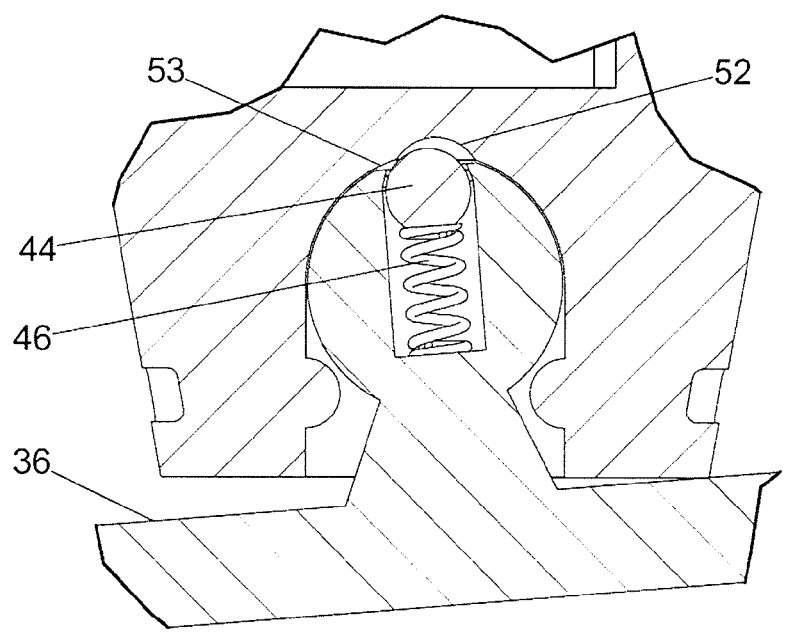
FIG. 7B illustrates an enlargement of the unlocked socket assembly of FIG. 7A.

FIG. 7A shows the release mechanism 51 of FIG. 6A in an unlocked position. FIG. 7B shows an enlargement of the unlocked release mechanism 51 of FIG. 7A. To unlock the release mechanism 51, the ball bearing 44 moves out of slot 52. Cylinder housing 20 (not shown) applies a pressure as at 53 in a longitudinal direction to the ball bearing 44 thereby compressing spring 46. The compressed spring 46 allows the ball bearing 44 to move out of slot 52, unlocking the release mechanism 51. The unlocked release mechanism 51 allows the testing head assembly 30 to pivot. Thus, the release mechanism 51 is structured and operable to be unlocked when the cylinder housing 20 applies longitudinal pressure 53 to the testing head assembly 30, resulting in the ball bearing 44 being positioned away from slot 52 allowing the testing head assembly 30 to pivot.

The unlocked release mechanism 51 permits the baseplate 36 to move out of the locked horizontal position and further allows the testing head assembly 30 to pivot from about one degree to about twenty degrees. In one embodiment, the testing head assembly 30 pivots in the range of about five degrees to about ten degrees. The ball bearing 44 connected to the spring 46 acts as a positive stop for the baseplate 36, which prevents the testing head assembly 30 from pivoting beyond a predetermined range. Thus, the testing head assembly 30 is structured and operable to pivot when the ball bearing 44 depresses the spring 46. Further, the testing head assembly 30 is structured and operable to pivot based on a minimal pressure 53 applied by the cylinder housing 20 to the testing head assembly 30, resulting in the ball bearing 44 compressing the spring 46, thereby allowing the testing head assembly 30 to pivot. Thus, the release mechanism 51 is structured and operable in a locked position when the ball bearing 44 is positioned within the slot 52, and the release mechanism 51 is structured and operable in an unlocked position when the ball bearing 44 is positioned away from the slot 52, that is, the ball bearing 44 is at least tangent to an arc 53.

Figure 8:
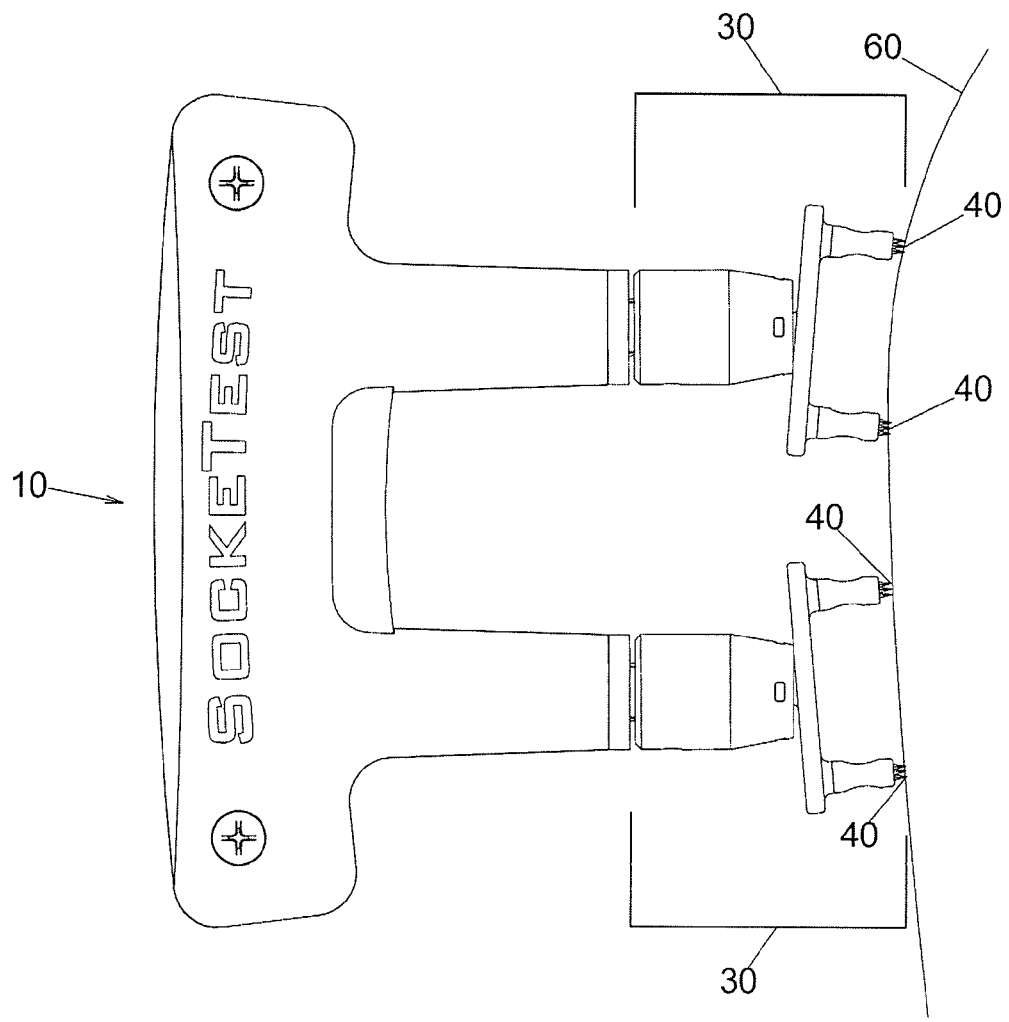
FIG. 8 shows the skin-testing device of FIG. 1 used on a back of a patient or animal.

FIG. 8 shows the skin-testing device 10 used on a back 60 of an animal or patient. As shown, the plurality of pins 40 is positionable against the skin. The back 60 is a curved structure. Therefore, when the release mechanism 51 is locked, the pressure applied to tips 40 of the testing head assembly 30 may not be equal or even. Thusly, when the tips 40 prick the surface of back 60, more pressure may be applied to one set of tips 40 and less pressure may be applied to another set of tips 40. Uneven pressure applied to various sets of tips 40 may vary the amount or volume of allergen applied to the skin, which may yield a false positive result. By unlocking the release mechanism 51, the socket assembly 50 pivots the testing head assembly 30. By pivoting the testing head assembly 30, an equal and even pressure is applied to all the tips or pins 40. The equal and even pressure applied to all the pins 40 eliminates false positive results.

Thus a method of testing patients to an allergen includes positioning the skin device 10 tangent to the surface of the skin 60, the device 10 having a handle assembly 12 connected to a cylinder assembly 20, the cylinder assembly 20 is structured and operable to attach to a plurality of testing head assemblies 30, wherein each testing head assembly includes a plurality of pins 40 structured to be coated with an allergen and to prick the surface of the skin 60, and a release mechanism 51 structured and operable to pivot the testing head assembly 30 and pivoting the testing head assembly 30 horizontally to apply equal and even pressure to the pins 40.

Figure 9A:
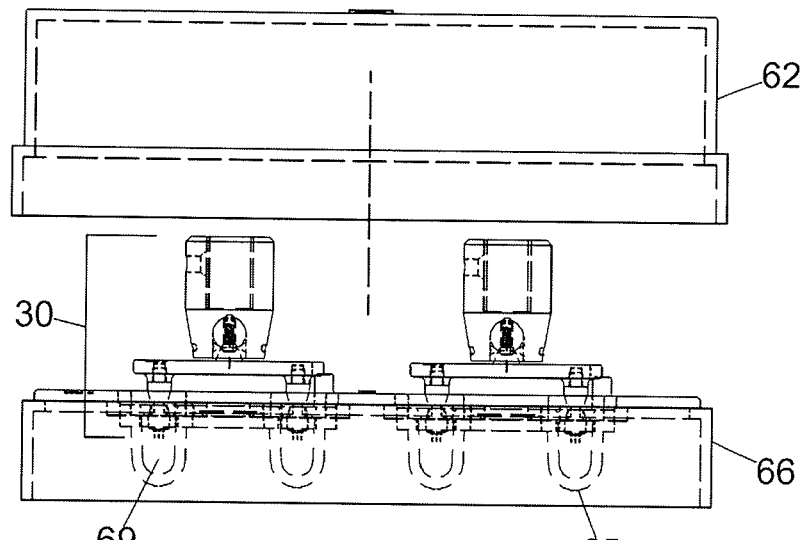
FIG. 9A describes a skin-testing kit.
Figure 9B:
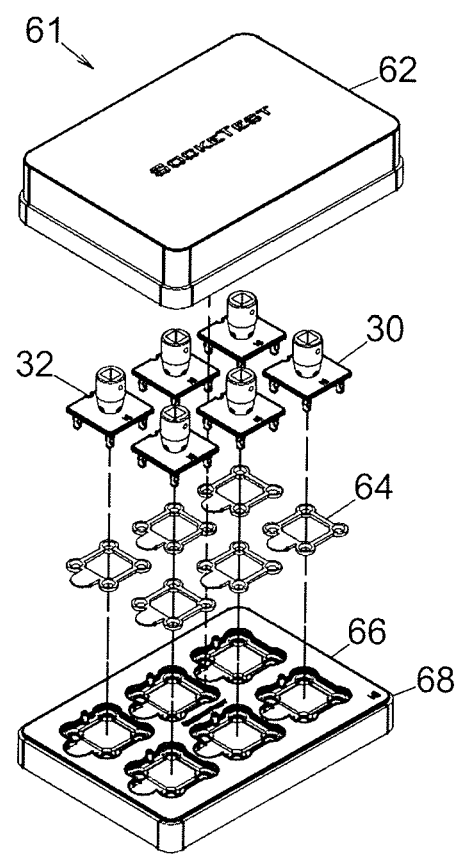
FIG. 9B shows an exploded view of the skin-testing kit.

FIG. 9A shows a skin testing kit, and FIG. 9B shows an exploded view of it. The skin testing kit 61 includes a plastic cover 62, the testing head assemblies 30, a plurality of inserts 64, and a dripwell tray 66. The cover includes the name Socketest® however, the cover is not restricted to that manufacturer. The wells 65 of the dripwell tray 66 are filled with at least one allergen 69. Each well 65 may contain different allergens 69. The insert 64 is structured and operably fits into the dripwell tray 66 to prevent the allergen 69 from spilling out of the dripwell tray 66. The testing head assemblies 30 couple to the insert 64 allowing the pins 34 and tips 40 of the testing head assembly 30 may be coated in the allergen 69. Over a predetermined period of time, the pins 34 and tips 40 are independently coated with a selected allergen.

The plastic cover 62 may be manufactured by injection molding of an impact resistant ABS plastic or another type of polymer that is lightweight and durable. The insert 64 and the dripwell tray 66 may be manufactured by injection molding of a polycarbonate or another type of clear impact resistant plastic. The dripwell tray 66 has a lip 68 that allows multiple dripwell trays 66 to stack on top of one another.

Figure 10:
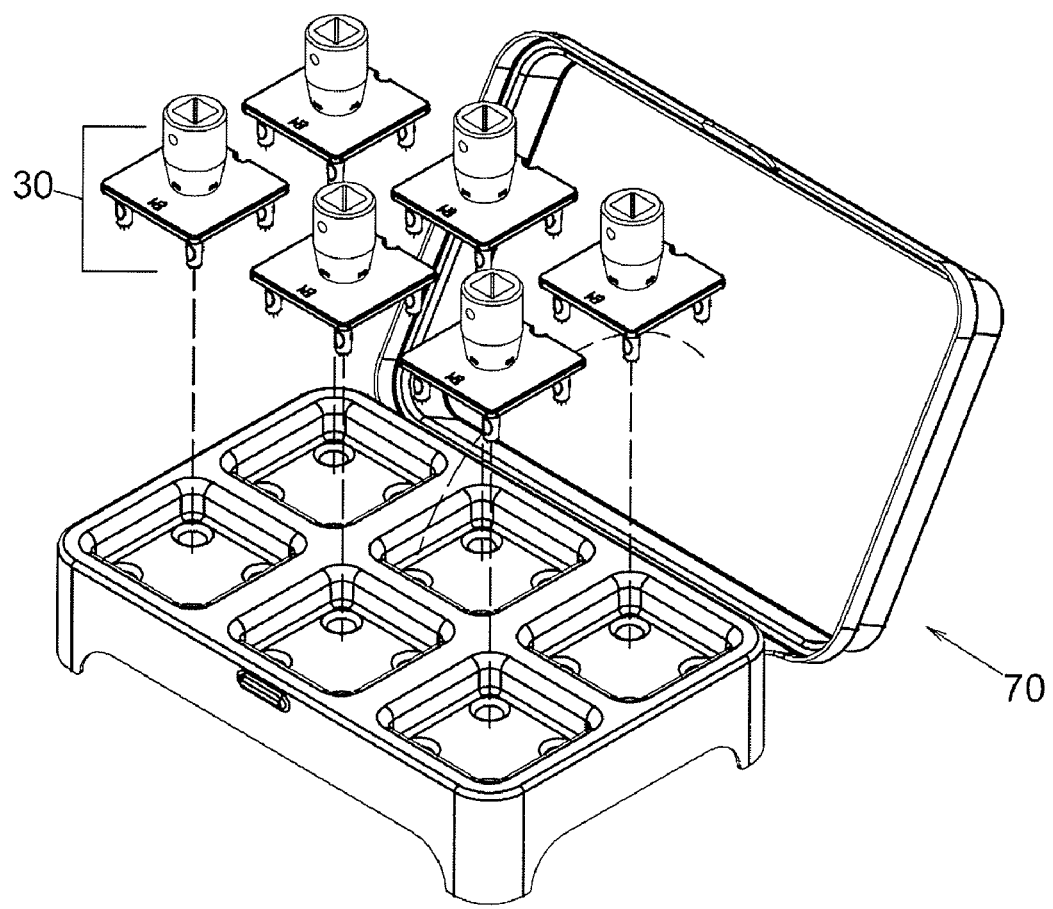
FIG. 10 shows an autoclave kit.

FIG. 10 shows an autoclave tray 70. The autoclave tray 70 may be manufactured from stainless steel metal (e.g., 18-gauge stainless steel). A plurality of testing head assemblies 30 fit into the autoclave tray 70 for sterilizing the testing head assemblies 30 before its reuse.

Figure 11:
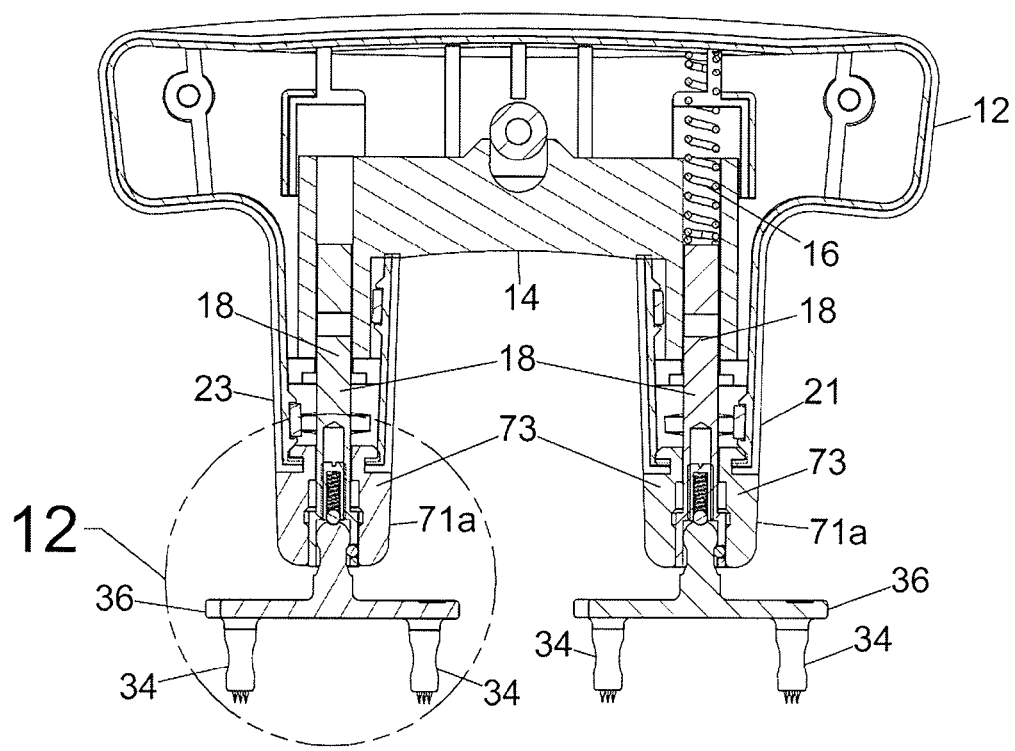
FIG. 11 has a sectional view of an alternate embodiment of the invention.
Figure 12:
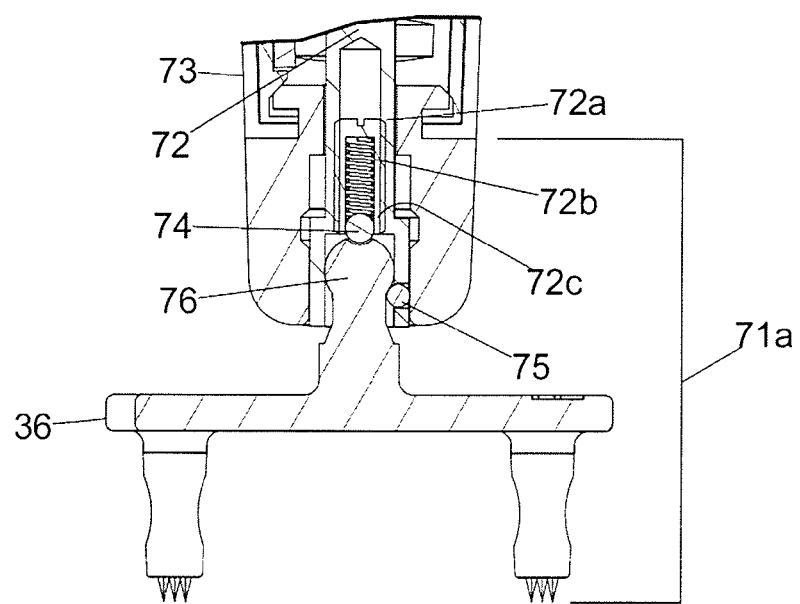
FIG. 12 provides a detailed view of one connection of a head to the handle of the alternate embodiment.

Another embodiment of the invention appears in FIG. 11 as a cross-section of the skin testing device 10 previously shown in FIG. 1 while FIG. 12 shows an enlarged view of a cylinder housing connected to a testing head assembly 71a shown in FIG. 11. As before, the handle 12 is connected to the cylinder assembly 20, the cylinder assembly 20 having two cylinder housings 21, 23 mutually parallel and spaced apart. These housings merge the socket into the handle of the previous embodiment.

The cylinder housings 21, 23 each have a removable connection to a testing head 36. Each cylinder housing includes a cylinder bearing shaft 18 threadily engaging a purchase set screw 72, later shown in FIG. 12. The cylinder bearing shaft 18 may be manufactured from high-grade stainless steel. The purchase set screw 72 has a structure to receive a rolling ball 74 positioned at the distal end of the shaft 18, that is, outwardly from the handle 12. The rolling ball 74 abuts the top of the head, as at 76, on the baseplate 36. The rolling ball 74 locates within a collar above the head unlike the previous embodiment that had the detent ball in the head itself. The rolling ball in the collar avoids the collection of detritus in the top of the head as in the previous embodiment.

Outwardly from the rolling ball, the collar has at least three balls 75 generally spaced about an opening in the collar that receives the top or ball hex 76 of the head 36. The rolling ball and hex balls appear similar to a 4 mm ball bearing and like bearings. The at least three balls operate as a quick release mechanism within the collar. The collar includes an internal biasing member that urges the at least three balls inwardly for retaining the ball hex 76 of the head but allows the at least three balls to move slightly outwardly for insertion of the ball hex into the quick release mechanism when in a locked position. This usage of at least three balls allows for insertion of the ball hex without depressing the trigger mechanism. A user disengages a ball hex and its test head by pulling the trigger as previously described, thus shifting the quick release mechanism to an unlocked position.

As before, the handle 12 still has its trigger mechanism 14 having a biasing device 16 (e.g., a spring, a pneumatic cylinder, and the like), where the biasing device 16 connects to the cylinder bearing shaft 18. The biasing device 16 may have high-grade stainless steel materials with a corrosion resistant grade of steel, and manufactured so that the biasing device 16 has the kinematic properties of a compression spring. The trigger mechanism 14 has its structure and operation so to compress the biasing device 16 such that the cylinder bearing shaft 18 presses the rolling ball 74 to separate the head 36 from the cylinder housing 21, 23.

In one embodiment, the testing head assembly 71a removes from the cylinder housing for its replacement by a user. For example, the testing head assembly 71a disconnects from the cylinder housing 21, 23 upon a user compressing the trigger mechanism 14 which causes the biasing device 16 to compress. The compressed biasing device 16 moves the cylinder bearing shaft 18 longitudinally along a vertical axis of the cylinder housing 71a, thereby resulting in the rolling ball 74 moving slightly outwardly against the head 36 for pushing the head outwardly from the housing.

FIG. 12 shows the connection of the head, as at 76, to the cylinder housing 21, 23 more closely for this alternate embodiment. The head assembly 71a has a head 76 connected to the end of a cylinder housing 21, 23. The cylinder housing extends downwardly from the handle into a cylindrical sleeve 73 having a generally hollow form with an opening 77 generally opposite the handle. Within the sleeve, the housing 21, 23 receives a purchase set screw 72 fitted snugly into the sleeve, preferably by a press fit or alternatively by adhesive.

The purchase set screw has a first end 72a having an internal spring 72b therein that receives the threaded end of the shaft 18. The internal spring extends over half way through the length of the purchase set screw and terminates in a smaller chamber 72c that admits the rolling ball 74 so that a portion of the rolling ball 74 abuts the shaft 18 without passing upwardly and outwardly through the smaller chamber.

Beneath the smaller chamber 72c and the internal spring 72b, the purchase set screw incorporates at least three balls 75 spaced about a hexagonal opening later shown in FIG. 14. The balls 75 accept the top 76 of the baseplate 36, or head, when inserted into the hexagonal opening and into the purchase set screw. The top 76 of the head then abuts the rolling ball 74 depending from the threaded shaft 18 as previously described. The rolling ball thus attains a contiguous position to the ball hex, particularly the top of the head.

Figure 13:
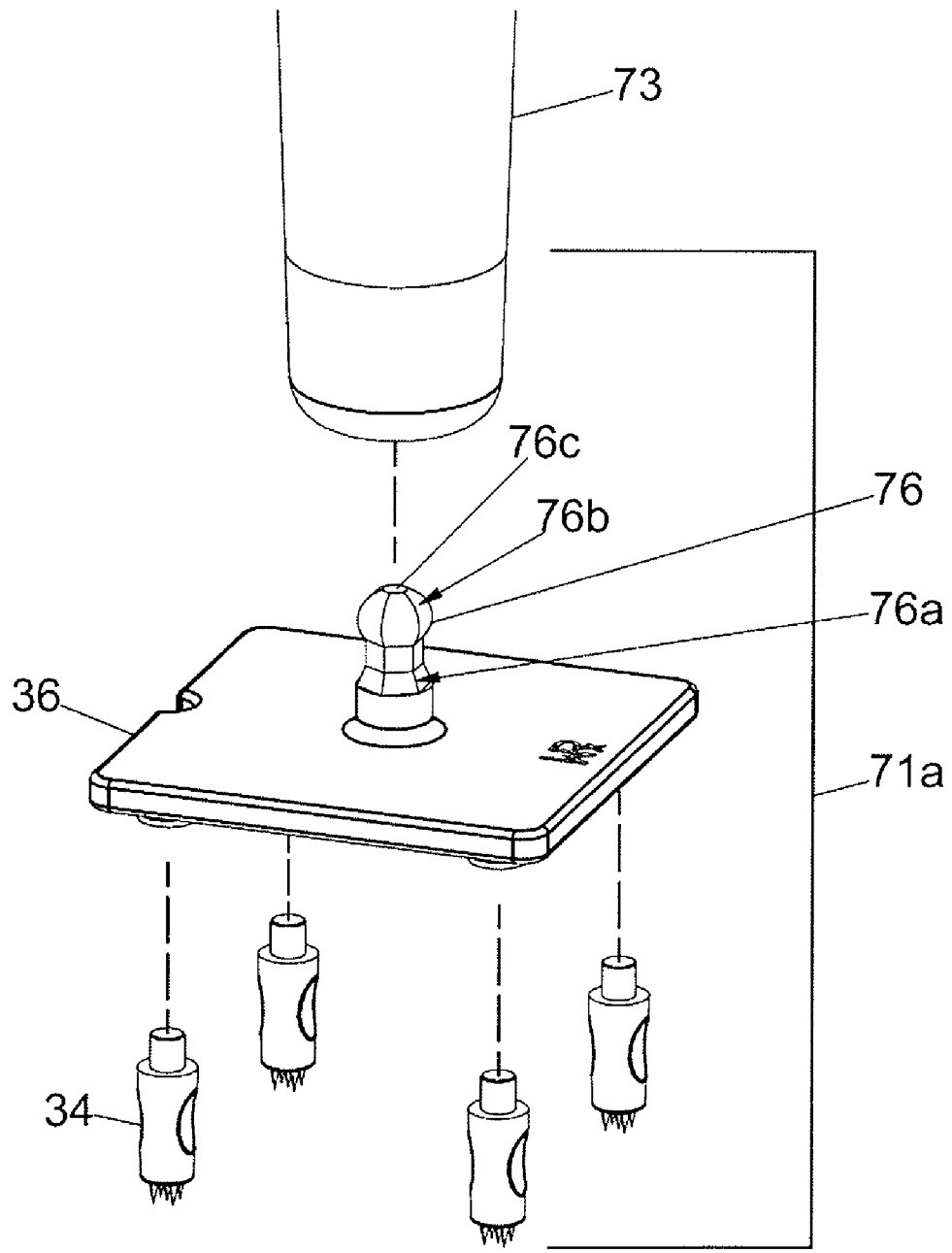
FIG. 13 illustrates an exploded view of one head of the alternate embodiment; and, FIG. 14 describes a bottom view of one handle of the alternate embodiment.

With the baseplate 36 spaced away from the sleeve 73 of the cylinder housing, FIG. 13 shows an exploded view of the testing head assembly 71a. As above, the testing head assembly 71a may have titanium, surgical-grade stainless steel, and like materials in its construction. The testing head assembly 71a may see reuse following sterilization or placement in an autoclave. Each testing head assembly 71a includes the sleeve 73, a baseplate 36 having a notch, and a ball hex denoting the top of the head as at 76. The ball hex 76 is a generally male like member that mates with the female like hexagonal opening, shown as 77 in FIG. 14. The baseplate 36 has a plurality of depending pins 34 connected to it for collection and application of allergens to a patient. The notch aligns the testing head assemblies 71a in an allergen tray as shown above in FIGS. 9, 10. The ball hex 76 has a pedestal 76a extending perpendicular to the baseplate and opposite the pins. The pedestal has a generally centered location upon the baseplate in line with the notch. Upon the pedestal, the ball hex has its ball portion 76b with a partial spheroid shape with six faces merging to a topmost circle 76c, or plane, that receives the rolling ball 74. Spaced above the ball hex 76, the sleeve includes the purchase set screw, balls, hexagonal opening, rolling ball, and threaded shaft within that accept the ball hex 76 upon insertion of a head of a baseplate 36 into the cylinder housing.

As previously shown in FIG. 5, a test head may turn upon three axes, axis-1 (e.g., corresponding to a z-axis), an axis-2 (e.g., corresponding to a x-axis), and an axis-0 (e.g., corresponding to a y-axis). The axes of movement 39 are in relation to the baseplate 36 generally positioned horizontally. Each testing head assembly 30 pivots along the axis-2, as indicated by arrows 33, 37 and along the axis-1, as indicated by arrows 31, 35. However, the ball portion 76b having six faces prevents rotation of the head about axis 1, that is the z-axis or y axis. The baseplate 36 with the ball hex 76 will not rotate about an axis coaxial with the length of a cylinder housing. The baseplate 36 will tip forward or rearward and leftward or rightward to accommodate the surface of a patient. The baseplate 36 though will not allow twisting which prevents injury to the skin of a patient.

Figure 14:
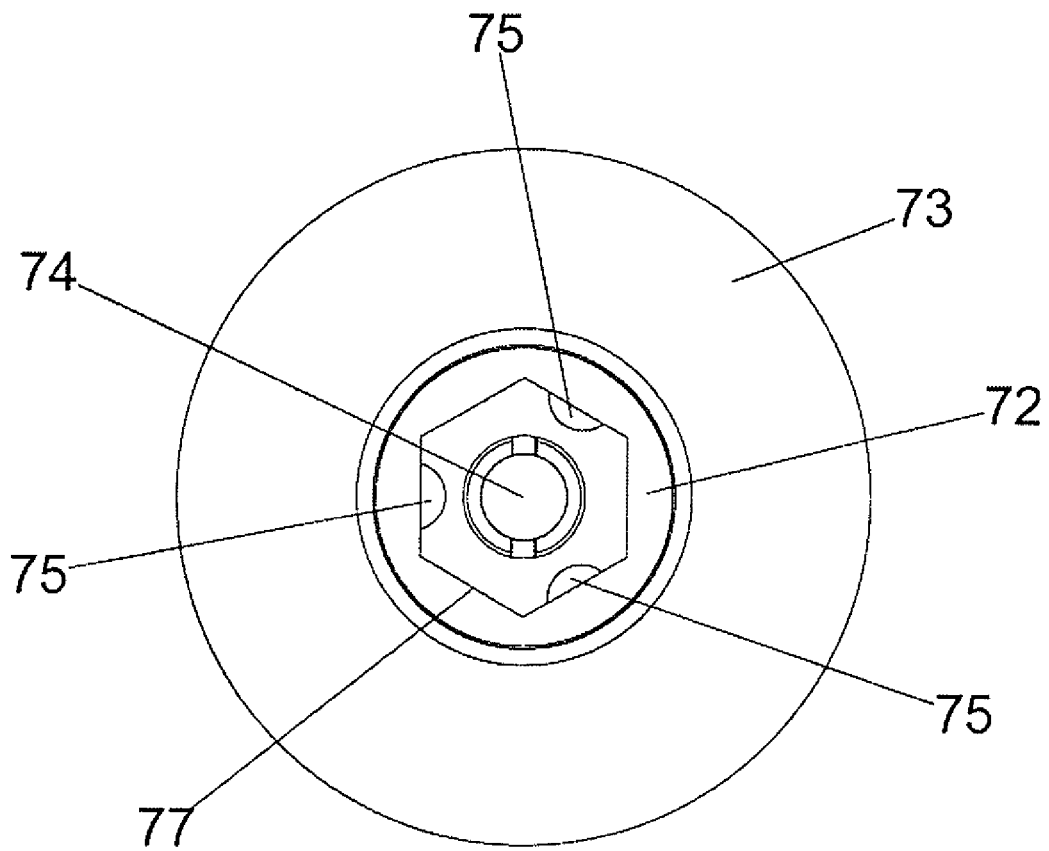

FIG. 14 shows the bottom of a handle, particularly a cylinder housing, as a user would view it prior to insertion of a ball hex 76 of a baseplate 36. In this view the housing has a generally round cross section formed of the sleeve 73 that surrounds the purchase set screw 72 and that has a hexagonally shaped opening 77. The opening 77 is slightly larger than the width of the ball hex to allow play of the ball hex upon only two axes. Within the opening 77, the purchase set screw includes at least three balls 75, generally equally spaced, forming a quick release mechanism, that accepts the ball hex 76 upon insertion generally below the ball portion 76b and proximate the pedestal.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

From the aforementioned description, a biaxial test head has been described. The device is uniquely capable of allowing a test head to pivot upon two axes only—that is without roll—thus preventing laceration to a patient, and lessens contamination of a test head from detritus contained within the handle and its component parts. The device applies allergens at a constant pressure from a user generally perpendicular to a patient's skin resulting in fewer false positives for allergy and a more comfortable patient. The biaxial test head provides a hexagonal ball tip upon a test head that fits within a hexagonal opening into the collar for restriction to biaxial movement. The device and its various components may be manufactured from many materials as described above but also generally, including but not limited to, polymers, steel, titanium, ferrous and non-ferrous metals, their alloys, select polymers, and composites. The Applicants recommend that ANSI fit specifications guide the manufacturing of running/sliding component interfaces where appropriate.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations have been described as multiple discrete operations, in turn, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to ascertain the nature of the technical disclosure, and with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

As such, those skilled in the art will appreciate that the conception, upon which this disclosure is based, may readily be utilized as a basis for the designing of other structures, methods and systems for carrying out the several purposes of the present invention. Heretofore, those skilled in the art have not recognized usage of ball hex shaped head for movement only upon two axes, a quick release mechanism, and the reduction in detritus retention within the device. Therefore, the claims include such equivalent constructions insofar as they do not depart from the spirit and the scope of the present invention.

We claim:

1. A biaxial device for testing allergens on the skin of a patient with fewer instances of false positives, said biaxial testing device comprising:
   a handle assembly connected to a cylinder assembly having two mutually parallel and spaced apart cylinder housings;
   each of said cylinder housings connecting to at least one testing head assembly;
   said at least one testing head assembly including a plurality of pins each having a plurality of tips adapted to position against the skin of a patient and a ball hex generally opposite said tips wherein said ball hex permits tipping of said head assembly only upon two axes thus applying equal and even pressure to said pins;
   a trigger mechanism within said handle assembly, said trigger mechanism including a biasing device connected to cylinder bearing shafts through each of said cylinder housings, each of said cylinder bearing shafts removably connecting to a testing head assembly;
   wherein a user may insert said ball hex of each testing head into said cylinder housing, use each testing head upon a patient, adjust each testing head only upon two axes, and then eject each testing head upon squeezing said trigger mechanism.

2. The biaxial testing device of claim 1 further comprising:
   each testing head having a generally rectangular planar shape with four edges and two opposite surfaces generally perpendicular to said edges, a notch upon one edge, said pins upon one surface and said ball hex having a centered location upon the other of said surfaces opposite said pins.

3. The biaxial testing device of claim 2 further comprising:
   each of said ball hexes having a partially spheroid shape having six equally spaced faces wherein the faces merge at a plane generally parallel to the other of said surfaces of said testing head and a pedestal locating below said spheroid shape, having six sides and lesser width than said tip.

4. The biaxial testing device of claim 1 further comprising:
   each of said cylinder housings including a hollow sleeve generally opposite said handle assembly, a hollow purchased set screw fitted within said sleeve, said purchased set screw having a first end proximate said handle assembly and an opposite second end away from said handle assembly, and said first end receiving said bearing shaft and an internal spring therein and said second end having an opening receiving said ball hex; and,
   said trigger mechanism having a structure and operation compressing said biasing device wherein each cylinder bearing shaft ejects a ball hex from each of said cylinder housings thus disconnecting said at least one testing head assembly from said device.

5. The biaxial testing device of claim 4 further comprising:
said second end including a quick release mechanism proximate said opening and a rolling ball inwardly from said opening and said quick release mechanism;
wherein said rolling ball abuts said ball hex upon insertion into said opening and abuts said cylinder bearing shaft.

6. The biaxial testing device of claim 5 further comprising:
said quick release mechanism having a locked position as said rolling ball has a position contiguous to said ball hex and said cylinder bearing shaft and an unlocked position as said rolling ball has a position contiguous to said cylinder bearing shaft;
said quick release mechanism having an unlocked position when said cylinder bearing shaft applies pressure to said rolling ball resulting in said ball hex being positioned outwardly from said opening;
said at least one testing head assembly pivoting upon pressure applied to it by said cylinder housing, resulting in said ball hex tipping within said opening, thereby allowing said testing head assembly to pivot only upon two axes.

7. The biaxial testing device of claim 3 further comprising:
said pins being independently coated with one of a plurality of allergens.

8. The device according to claim 1 wherein said testing head assembly is reusable and at least one of sterilized and autoclaved.

9. The biaxial testing device of claim 4 further comprising:
said opening in said second end having a hexagonal shape to receive said ball hex.

10. A biaxial device for testing allergens on the skin of a patient minimizing false positives, said biaxial testing device comprising:
a handle assembly connected to a cylinder assembly having two mutually parallel and spaced apart cylinder housings;
each of said cylinder housings connecting to at least one testing head assembly, said at least one testing head assembly including a plurality of pins each having a plurality of tips adapted to position against the skin of a patient and a ball hex generally opposite said tips wherein said ball hex permits tipping of said head assembly only upon two axes thus applying even pressure to said pins, each testing head having a generally rectangular planar shape with four edges and two opposite surfaces generally perpendicular to said edges, a notch upon one edge, said pins upon one surface and said ball hex having a centered location upon the other of said surfaces opposite said pins;
a trigger mechanism positioning within said handle assembly and including a biasing device connected to cylinder bearing shafts through each of said cylinder housings, each of said cylinder bearing shafts removably connecting to a testing head assembly;
each of said ball hexes having a partially spheroid shape having six equally spaced faces wherein the faces merge at a plane generally parallel to the other of said surfaces of said testing head and a pedestal having six sides and a lesser width than said tip, and said pedestal locating beneath said spheroid shape;
each of said cylinder housings including a hollow sleeve generally opposite said handle assembly, a hollow purchased set screw fitted within said sleeve, said purchased set screw having a first end proximate said handle assembly and an opposite second end away from said handle assembly, and said first end receiving said bearing shaft and an internal spring and said second end having an opening receiving said ball hex;
said trigger mechanism having a structure and operation compressing the biasing device wherein each cylinder bearing shaft ejects a ball hex from each of said cylinder housings thus disconnecting said testing head assembly from said device;
said second end including a quick release mechanism proximate said opening and a rolling ball inwardly from said opening and said quick release mechanism; wherein said rolling ball abuts said ball hex upon insertion into said opening and abuts said cylinder bearing shaft;
said quick release mechanism having:
a locked position as said rolling ball has a position contiguous to said ball hex and said cylinder bearing shaft; and,
an unlocked position as said rolling ball has a position contiguous to said cylinder bearing shaft when said cylinder bearing shaft applies pressure to said rolling ball resulting in said ball hex being positioned outwardly from said opening;
said at least one testing head assembly pivoting upon pressure applied to it by said cylinder housing, resulting in said ball hex tipping within said opening, thereby allowing said testing head assembly to pivot only upon two axes;
wherein a user may insert said ball hex of each testing head, use each testing head upon a patient, adjust each testing head upon two axes, and then eject each testing head upon squeezing said trigger mechanism;
wherein said pins are independently coated with one of a plurality of allergens;
wherein said testing head assembly is reusable and can be at least one of sterilized and autoclaved.

11. The biaxial testing device of claim 10 further comprising:
said opening in said second end having a hexagonal shape to receive said ball hex.

* * * * *